United States Patent
Simpson

(10) Patent No.: US 10,022,159 B2
(45) Date of Patent: Jul. 17, 2018

(54) SURGICAL INSTRUMENT AND METHOD

(71) Applicant: Warsaw Orthopedic, Inc., Warsaw, IN (US)

(72) Inventor: Joshua W. Simpson, Collierville, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 38 days.

(21) Appl. No.: 14/974,818

(22) Filed: Dec. 18, 2015

(65) Prior Publication Data

US 2017/0172633 A1   Jun. 22, 2017

(51) Int. Cl.
*A61B 17/70* (2006.01)
*A61B 17/88* (2006.01)
*A61B 17/00* (2006.01)

(52) U.S. Cl.
CPC ...... *A61B 17/7053* (2013.01); *A61B 17/8869* (2013.01); *A61B 2017/00407* (2013.01)

(58) Field of Classification Search
CPC .................................................. A61B 17/7053
See application file for complete search history.

(56) References Cited

U.S. PATENT DOCUMENTS

| | | | | |
|---|---|---|---|---|
| 5,964,769 A * | 10/1999 | Wagner | ................... | A61B 17/82 606/103 |
| 6,146,386 A * | 11/2000 | Blackman | .......... | A61B 17/7079 606/103 |
| 6,689,140 B2 | 2/2004 | Cohen | | |
| 8,113,410 B2 * | 2/2012 | Hall | ................. | A61B 17/07207 227/176.1 |
| 8,162,946 B2 * | 4/2012 | Baccelli | ............. | A61B 17/8869 606/263 |
| 8,216,245 B2 * | 7/2012 | Gil | ..................... | A61B 17/7022 606/103 |
| 8,323,294 B2 * | 12/2012 | Mickiewicz | ......... | A61B 17/701 606/101 |
| 8,728,083 B2 * | 5/2014 | Baccelli | ............. | A61B 17/7053 606/86 A |
| 8,932,296 B2 * | 1/2015 | Neary | ................ | A61B 17/7077 606/86 A |
| 9,757,167 B2 * | 9/2017 | Hsu | ..................... | A61B 17/7076 |
| 9,763,731 B2 * | 9/2017 | Dubois | ............ | A61B 17/32002 |
| 2002/0072753 A1 * | 6/2002 | Cohen | ................. | A61B 17/8861 606/103 |
| 2002/0198538 A1 * | 12/2002 | Kortenbach | .......... | A61B 17/122 606/139 |
| 2005/0070958 A1 * | 3/2005 | Swayze | ............ | A61B 17/07207 606/219 |
| 2005/0154403 A1 * | 7/2005 | Sauer | ................. | A61B 17/0469 606/139 |
| 2009/0054933 A1 * | 2/2009 | Mickiewicz | ....... | A61B 17/8869 606/86 A |
| 2015/0164561 A1 * | 6/2015 | Simpson | ............ | A61B 17/7002 606/264 |

* cited by examiner

*Primary Examiner* — Ellen C Hammond
*Assistant Examiner* — Stuart S Bray

(57) ABSTRACT

A surgical instrument comprises a first member that defines a cavity and includes a locking surface disposed with the cavity. The locking surface is engageable with a longitudinal member to fix the longitudinal member with the first member. A second member includes at least one mating element that is engageable with a spinal construct. An actuator is connected with the members that incrementally tensions the longitudinal member. Systems, implants and methods are disclosed.

20 Claims, 19 Drawing Sheets

SURGICAL INSTRUMENT AND METHOD

TECHNICAL FIELD

The present disclosure generally relates to medical devices for the treatment of spinal disorders, and more particularly to a surgical instrument and method for correction of a spine disorder.

BACKGROUND

Spinal disorders such as degenerative disc disease, disc herniation, osteoporosis, spondylolisthesis, stenosis, scoliosis and other curvature abnormalities, kyphosis, tumor, and fracture may result from factors including trauma, disease and degenerative conditions caused by injury and aging. Spinal disorders typically result in symptoms including pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, fusion, fixation, discectomy, laminectomy and implantable prosthetics. As part of these surgical treatments, spinal constructs, which include implants such as tethers, bone fasteners, connectors, plates and vertebral rods are often used to provide stability to a treated region. These implants can redirect stresses away from a damaged or defective region while healing takes place to restore proper alignment and generally support the vertebral members. Surgical instruments are employed, for example, to engage the implants for attachment to the exterior of one or more vertebral members. This disclosure describes an improvement over these prior technologies.

SUMMARY

In one embodiment, a surgical instrument is provided. The surgical instrument comprises a first member that defines a cavity and includes a locking surface disposed with the cavity. The locking surface is engageable with a longitudinal member to fix the longitudinal member with the first member. A second member includes at least one mating element that is engageable with a spinal construct. An actuator is connected with the members that incrementally tensions the longitudinal member. In some embodiments, systems, implants and methods are disclosed.

BRIEF DESCRIPTION OF THE DRAWINGS

The present disclosure will become more readily apparent from the specific description accompanied by the following drawings, in which.

DETAILED DESCRIPTION

Figure 1:
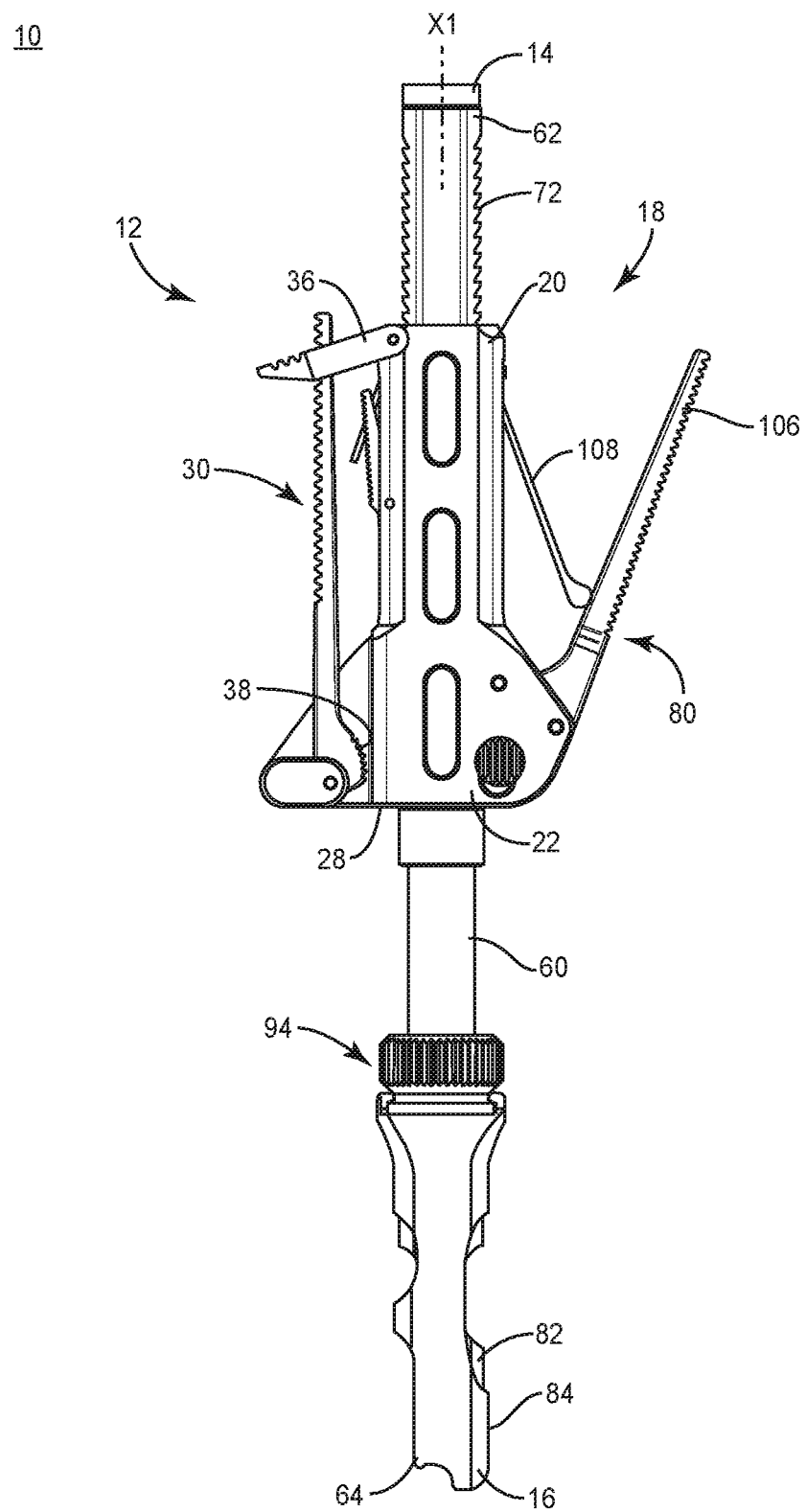
FIG. 1 is a side view of one embodiment of components of a surgical system in accordance with the principles of the present disclosure.

The exemplary embodiments of a surgical system and related methods of use are discussed in terms of medical devices for the treatment of musculoskeletal disorders and more particularly, in terms of a surgical system and method for correction of a spine disorder. In some embodiments, the surgical system may be employed in applications for correction of deformities, such as scoliosis and kyphosis.

In some embodiments, the surgical system includes a surgical instrument that comprises a tether tensioner. In some embodiments, the surgical system includes a surgical instrument that comprises a sub-laminar tether tensioner. In some embodiments, the surgical system provides a tensioner for providing tension to a tether portion of a connector. In some embodiments, the surgical system includes a surgical instrument that provides, for example, loading one or more implants of a spinal construct, for example, a connector to a spinal rod and into a body; affixing a connector to a spinal rod and providing counter-torque to tighten a set screw; and tensioning a tether. In some embodiments, the surgical instrument includes a ratcheting mechanism to tension a tether. In some embodiments, the surgical instrument includes a threaded mechanism to tension a tether.

In some embodiments, the surgical system is employed with a method that includes the step of reducing a spinal rod to a spine and applying tension to a sub-laminar tether. In some embodiments, the method includes the step employing a surgical tensioner instrument to reduce the spinal rod and apply tension to the sub-laminar tether. In some embodiments, the surgical instrument includes a ratcheting tensioner that uses teeth and a pawl to move a carriage away from a spinal construct while pulling a tether. In some embodiments, the surgical instrument includes a threaded tensioner. In some embodiments, the surgical instrument includes a threaded tensioner that moves a threaded carriage away from a spinal construct while drawing a tether.

In some embodiments, the surgical instrument includes a ratcheting tensioner that includes a ratcheting mechanism. In some embodiments, the ratcheting tensioner includes a catch that resists and/or prevents a carriage from translating downward while a pawl resets. In some embodiments, the catch cannot be released while a cam lever arm of the ratcheting mechanism is engaged, which resists and/or prevents accidental release of the carriage while a tether is under tension.

In some embodiments, the ratcheting tensioner includes a lever that drives the pawl downward, forcing the carriage upward. In some embodiments, a single actuation or engagement, for example, squeezing of the lever produces translation of the carriage. In some embodiments, a single actuation of the lever produces 1.5 millimeters (mm) of translation of the carriage. In some embodiments, the ratcheting tensioner includes a cam lock to attach the carriage with a tether. In some embodiments, the ratcheting tensioner includes a safety latch that resists and/or prevents disengagement of the tether from the carriage. In some embodiments, the ratcheting tensioner includes a carriage that defines a tether path.

In some embodiments, the surgical instrument includes one or more locks to fix a spinal rod and/or a connector with the tensioner. In some embodiments, the surgical instrument includes one or more tabs to lock the surgical instrument to a connector. In some embodiments, the surgical instrument includes an outer sleeve that resists and/or prevents the tabs from releasing the connector. In some embodiments, the surgical instrument includes an outer sleeve that locks a spinal rod in position.

In some embodiments, the surgical system includes a surgical instrument configured to apply a tension to a sub-laminar tether. In some embodiments, the surgical system includes a tensioner configured to apply a tension to a tether and/or a spinal construct. In some embodiments, the tensioner is configured for attachment with a spinal construct, such as, for example, a connector. In some embodiments, the tensioner is configured for attachment with the connector via mating surfaces. In some embodiments, the mating surfaces include one or more slots. In some embodiments, the tensioner includes a mating element for engagement with slots disposed with the connector. In some embodiments, the tensioner comprises an implant holder.

In some embodiments, the surgical system includes a tether configured for engagement with the connector. In some embodiments, the surgical instrument includes a threaded shaft to facilitate translation of a carriage in a direction away from the connector by rotation along a threaded shaft. In some embodiments, the surgical instrument includes a knob to actuate translation and apply a tension to the tether.

In some embodiments, the surgical system includes one or more implants, such as, for example, a sub-laminar tether and a connector. In some embodiments, the surgical system includes one or more surgical instruments, such as, for example, a tensioner, a socket driver and a counter-torque handle. In some embodiments, the tether includes a tip having a 90 millimeter (mm) length to facilitate passage under a lamina. In some embodiments, the tether includes a 750 mm length to facilitate wrapping of the tether about the tensioner.

In some embodiments, the surgical system includes a connector having slots configured to facilitate connection of the connector with a surgical instrument. In some embodiments, the slots provide visual indicia of the connector for mating and/or docking with a surgical instrument. In some embodiments, the slots provide access to a top surface of the connector by a surgical instrument to control axial translation and facilitate engagement of the surgical instrument therewith. In some embodiments, the tether is connected with the connector by a screw similar to a screw utilized for connection of the connector with a spinal rod. In some embodiments, the surgical system includes a t25 torx screw for connection of the connector with a spinal rod and a t25 torx screw for connecting the tether with the connector.

In some embodiments, the surgical system includes a tensioner connected with a spinal rod such that the tensioner engages along a surface of the spinal rod and/or has a run on the spinal rod of 25 mm. In some embodiments, the surgical system includes a tensioner having a medial-lateral width of 25 mm. In some embodiments, the surgical system includes a tensioner having a member including a triple lead thread. In some embodiments, the triple lead thread is configured to provide for increase in advancement time of a carriage with a decrease in mechanical advantage. In some embodiments, the carriage is configured to translate 9.5 mm per rotation and includes 75 mm of thread length. In some embodiments, indicia, such as, for example, hash marks are provided on the member as a reference guide. In some embodiments, the carriage includes a cam lock having a decreased length and a larger actuation surface for manipulation.

In some embodiments, the surgical system includes a tensioner having a projection configured to straighten tension on the tether. In some embodiments, the projection is configured to resist and/or prevent the tether from contacting sharp surfaces. In some embodiments, the surgical system includes a socket driver. In some embodiments, the socket driver is configured to provide additional torque to facilitate tensioning. In some embodiments, the socket driver is configured to provide segmental tensioning if multiple tensioners are utilized. In some embodiments, the surgical system includes a counter-torque handle engageable with the tensioner. In some embodiments, the counter-torque handle is configured to facilitate fracturing break off portions of set screws.

In some embodiments, the surgical system is used with surgical navigation, such as, for example, fluoroscope or image guidance. In some embodiments, one or all of the components of the surgical system are disposable, peel-pack, pre-packed sterile devices. One or all of the components of the surgical system may be reusable. The surgical system may be configured as a kit with multiple sized and configured components.

In some embodiments, the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the present disclosure may be employed with other osteal and bone related applications, including those associated with diagnostics and therapeutics. In some embodiments, the disclosed surgical system and methods may be alternatively employed in a surgical treatment with a patient in a prone, supine position, lateral and/or employ various surgical approaches to the spine, including anterior, posterior, posterior mid-line, direct lateral, postero-lateral, and/or antero-lateral approaches, and in other body regions. The present disclosure may also be alternatively employed with procedures for treating the lumbar, cervical, thoracic, sacral and pelvic regions of a spinal column. The system and methods of the present disclosure may also be used on animals, bone models and other non-living substrates, such as, for example, in training, testing and demonstration.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, micro discectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. As used in the specification and including the appended claims, the term "tissue" includes soft tissue, ligaments, tendons, cartilage and/or bone unless specifically referred to otherwise.

The following discussion includes a description of a surgical system and related methods of employing the surgical system in accordance with the principles of the present disclosure. Alternate embodiments are also disclosed. Reference is made in detail to exemplary embodiments of the present disclosure, which are illustrated in the accompanying figures. Turning to FIGS. 1-9, there are illustrated components of a surgical system, such as, for example, a spinal correction system 10.

The components of spinal correction system 10 can be fabricated from biologically acceptable materials suitable for medical applications, including metals, synthetic polymers, ceramics and bone material and/or their composites. For example, the components of spinal correction system 10, individually or collectively, can be fabricated from materials such as stainless steel alloys, commercially pure titanium, titanium alloys, Grade 5 titanium, super-elastic titanium alloys, cobalt-chrome alloys, superelastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate such as hydroxyapatite (HA), corraline HA, biphasic calcium phosphate, tricalcium phosphate, or fluorapatite, tri-calcium phosphate (TCP), HA-TCP, calcium sulfate, or other resorbable polymers such as polyaetide, polyglycolide, polytyrosine carbonate, polycaroplaetohe and their combinations, biocompatible ceramics, mineralized collagen, bioactive glasses, porous metals, bone particles, bone fibers, morselized bone chips, bone morphogenetic proteins (BMP), such as BMP-2, BMP-4, BMP-7, rhBMP-2, or rhBMP-7, demineralized bone matrix (DBM), transforming growth factors (TGF, e.g., TGF-β), osteoblast cells, growth and differentiation factor (GDF), insulin-like growth factor 1, platelet-derived growth factor, fibroblast growth factor, or any combination thereof.

Various components of spinal correction system 10 may have material composites, including the above materials, to achieve various desired characteristics such as strength, rigidity, elasticity, compliance, biomechanical performance, durability and radiolucency or imaging preference. The components of spinal correction system 10, individually or collectively, may also be fabricated from a heterogeneous material such as a combination of two or more of the above-described materials. The components of spinal correction system 10 may be monolithically formed, integrally connected or include fastening elements and/or instruments, as described herein.

Spinal correction system 10 comprises a surgical instrument, such as, for example, a tensioner 12. Tensioner 12 extends between an end 14 and an end 16. Tensioner 12 defines a longitudinal axis X1. In some embodiments, tensioner 12 may comprise overall and/or cross-section configurations, such as, for example, cylindrical, round, oval, rectangular, polygonal, irregular, tapered, offset, staggered, uniform and non-uniform. In some embodiments, one or more of the surfaces of tensioner 12 may have alternate surface configurations, such as, for example, rough, threaded for connection with surgical instruments, arcuate, undulating, porous, semi-porous, dimpled, polished and/or textured.

Tensioner 12 includes a member or first member, such as, for example, a carriage 18. Carriage 18 extends between an end 20 and an end 22. In some embodiments, carriage 18 may have various configurations, for example, circular, cylindrical, square, oval, rectangular, polygonal, irregular, tapered, offset, staggered and uniform. Carriage 18 includes an outer surface 24. In some embodiments, outer surface 24 may have alternate surface configurations, such as, for example, smooth, rough, threaded for connection with surgical instruments, arcuate, undulating, porous, semi-porous, dimpled, polished and/or textured.

Figure 3:
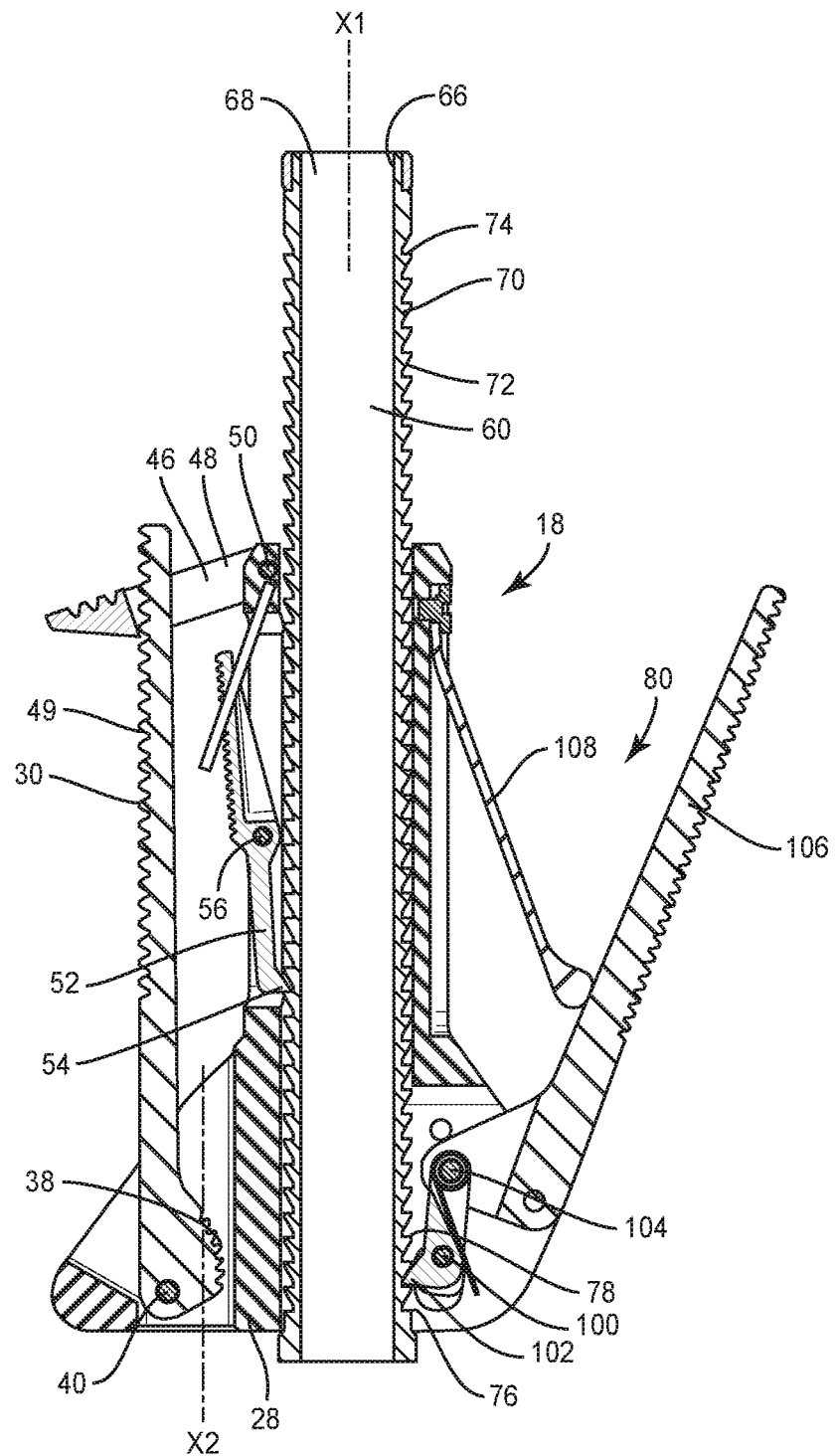
FIG. 3 is a cross section view of the components shown in FIG. 2.
Figure 4:
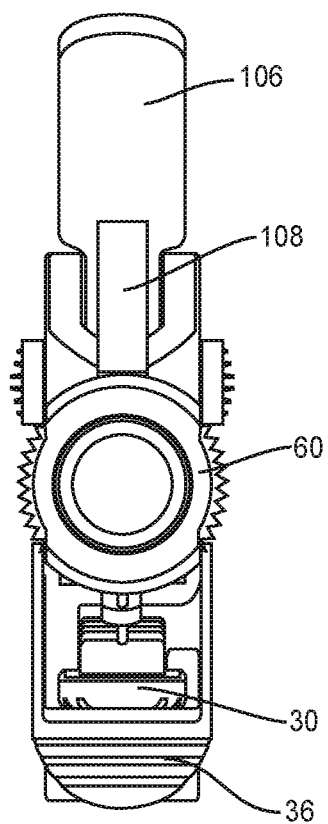
FIG. 4 is an end view of the components shown in FIG. 1.
Figure 5:
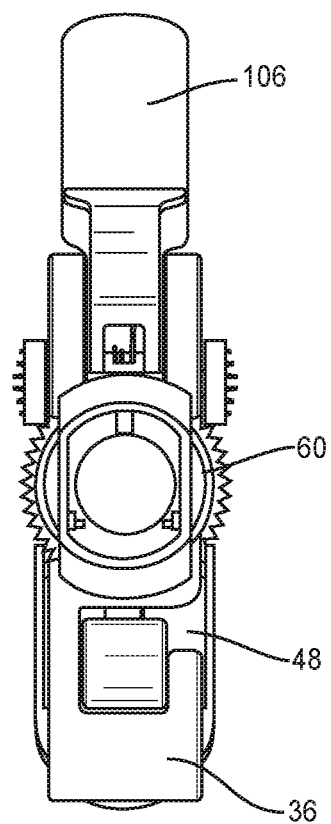
FIG. 5 is an end view of the components shown in FIG. 1.
Figure 10:
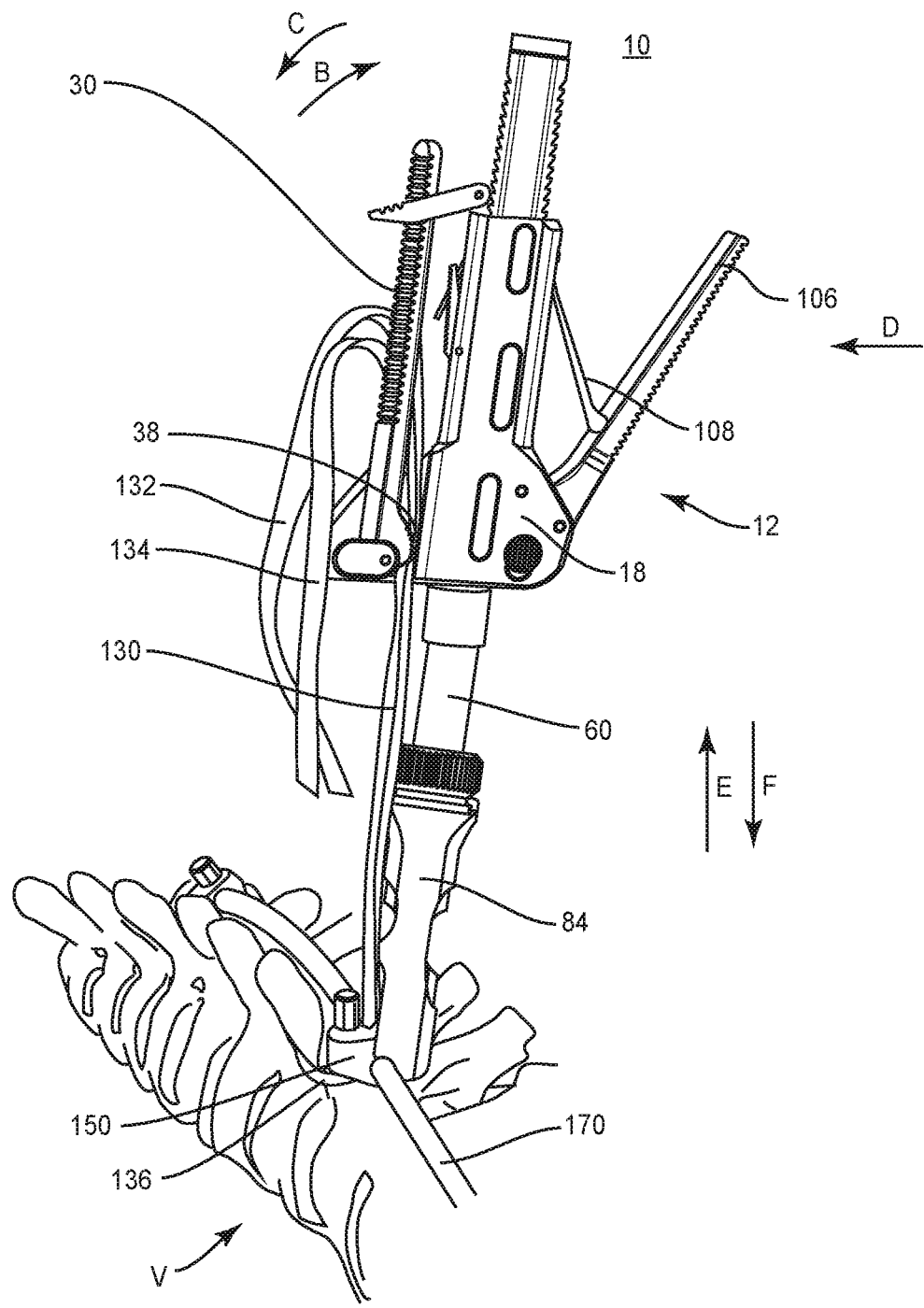
FIG. 10 is a perspective view of one embodiment of components of a surgical system in accordance with the principles of the present disclosure disposed with vertebrae.

Carriage 18 includes a surface 26 that defines an elongated cavity, such as, for example, a pathway 28 that defines a longitudinal member path. Pathway 28 is configured for disposal of a longitudinal member, such as, for example, a tether 130 (FIG. 10). In some embodiments, pathway 28 extends along an axis X2, as shown in FIG. 3. In some embodiments, axis X2 is parallel to axis X1. In some embodiments, axis X2 extends transverse to axis X1. In some embodiments, pathway 28 may have various cross sectional and/or axial configurations, for example, square, oval, rectangular, polygonal, irregular, offset, staggered, uniform and non-uniform.

Carriage 18 includes an arm, such as, for example, a lever 30. Lever 30 extends between an end 32 and an end 34. End 32 is configured for engagement with a lock, such as, for example, a latch 36, as described herein. End 34 includes a rotatable cam, such as, for example, a locking surface 38. Lever 30 is configured to pivot relative to axis X2 about a pin 40 disposed with end 34. Pin 40 is configured to facilitate engagement of locking surface 38 with tether 130. Locking surface 38 is in communication with pathway 28 such that locking surface 38 engages tether 130 to resist and/or prevent disengagement of tether 130 from pathway 28. In some embodiments, locking surface 38 is angled to facilitate engagement of tether 130 in a locked orientation, as described herein. In some embodiments, locking surface 38 may include penetrating members, such as, for example, a plurality of teeth 42. In some embodiments, teeth 42 may have various configurations, for example, round, oval, rectangular, polygonal, irregular, tapered, offset, staggered, uniform and non-uniform.

Figure 2:
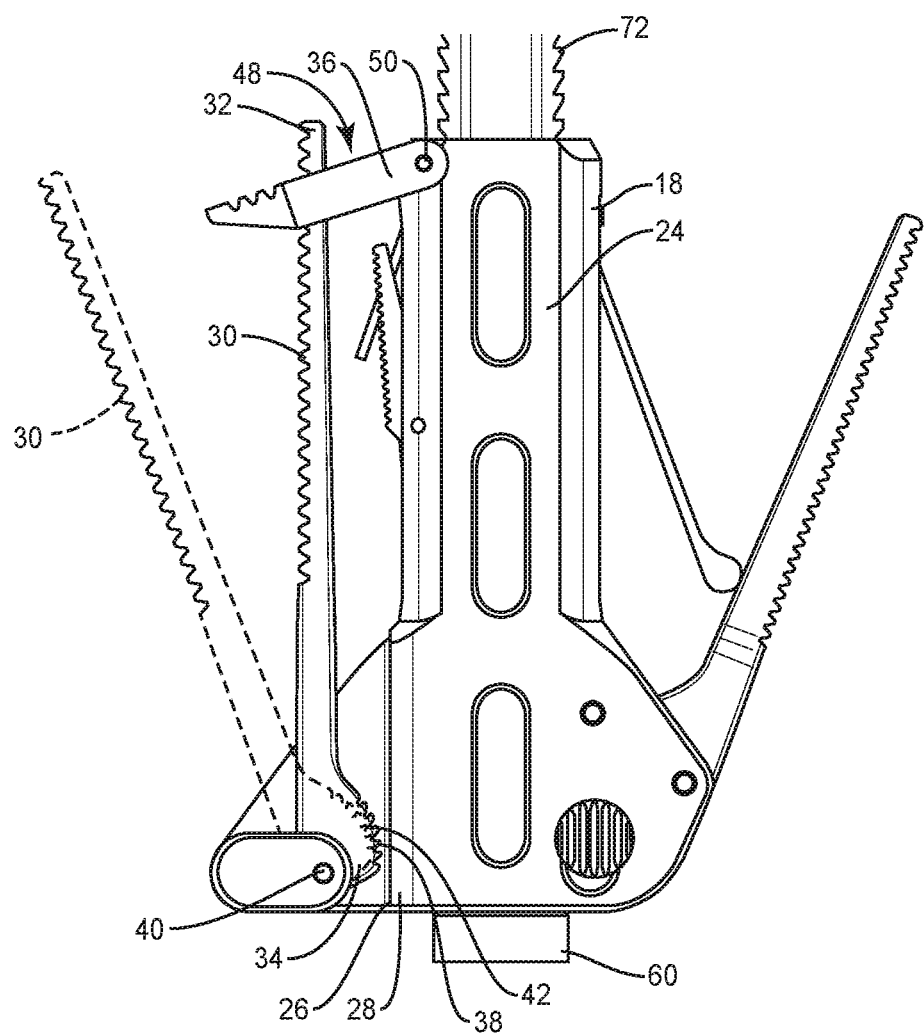
FIG. 2 is a break away side view, in part phantom, of the components shown in FIG. 1.

Rotation of lever 30 causes locking surface 38 to pivot between a non-locked orientation and a locked orientation with tether 130, as shown in FIG. 2. In the locked orientation, teeth 42 engage tether 130 to fix tether 130 with carriage 18. Locking surface 38 applies a compressive force and/or a friction force, as described herein, to fix tether 130 in the locked orientation. Locking surface 38 is configured for engagement with tether 130 to resist and/or prevent disengagement of tether 130 from pathway 28.

Latch 36 extends from surface 24. Latch 36 includes a surface 46 that defines a cavity 48. Cavity 48 is configured for disposal of lever 30 to fix lever 30 in the locked orientation and fix cam position of locking surface 38 with tether 130. In some embodiments, lever 30 includes a plurality of teeth 49 configured to facilitate selective positioning of latch 36 relative to lever 30. Latch 36 is configured to pivot about a pin 50. Pin 50 is configured to facilitate locking and un-locking of latch 36 with lever 30. In some embodiments, latch 36 extends transverse to axis X1. In some embodiments, latch 36 may have various configurations, such as, for example, square, oval, rectangular, polygonal, irregular, offset, staggered, uniform and non-uniform.

In some embodiments, carriage 18 includes a pivoting catch 52. Pivoting catch 52 includes a gear tooth 54. Gear tooth 54 is configured for engagement with gear teeth 78 of a rack 72 of a second member, such as, for example, a member 60, as described herein. Pin 56 connects pivoting catch 52 with latch 36. Pivoting catch 52 is rotatable relative to member 60 such that pivoting catch 52 pivots about pin 56 causing gear tooth 54 to move into engagement with gear teeth 78 to facilitate translation in a first direction and resist and/or prevent translation in a second direction, as described herein.

Figure 6:
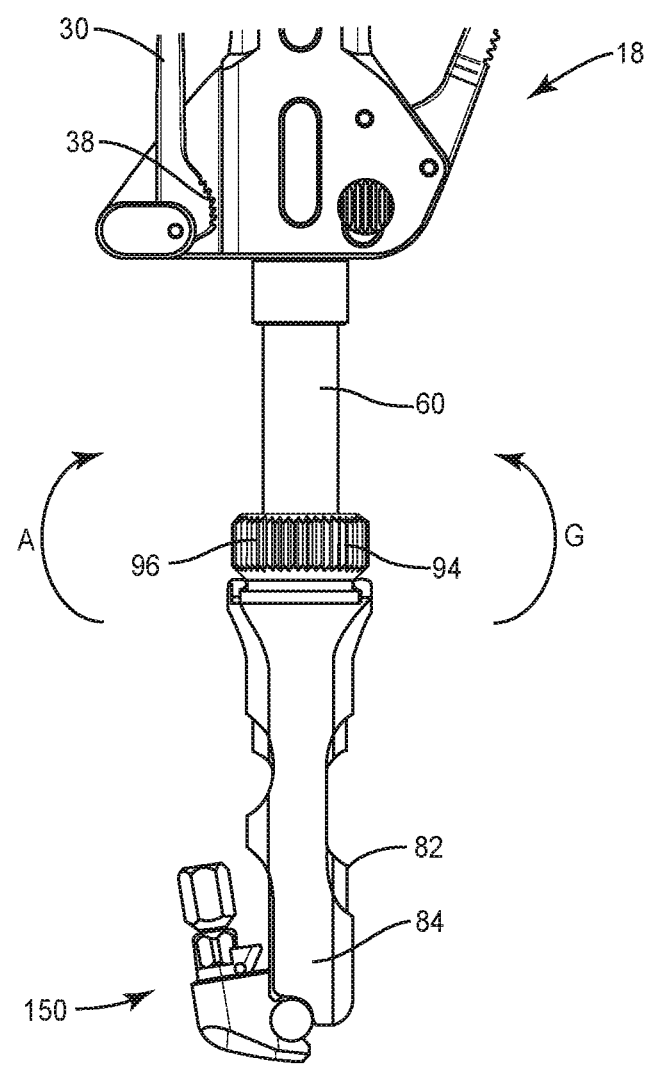
FIG. 6 is a break away side view of one embodiment of components of a surgical system in accordance with the principles of the present disclosure.

Member 60 extends between an end 62 and an end 64. Member 60 includes a surface 66 that defines a cavity, such as, for example, a channel 68. Channel 68 is configured for disposal of a surgical instrument, such as, for example a driver (not shown) to facilitate engagement with a spinal implant, such as, for example, a connector 150 (FIG. 6). In some embodiments, channel 68 may have various cross section and/or axial configurations, for example, round, oval, rectangular, polygonal, irregular, tapered, offset, staggered, uniform and non-uniform.

Member 60 includes a surface 70. Surface 70 includes rack 72. Rack 72 extends between an end 74 and an end 76. Rack 72 includes a plurality of gear teeth 78 configured for engagement with a pawl 100, as described herein. Rack 72 is configured as a portion of an actuator, such as, for example, a ratchet 80, as described herein. In some embodiments, surface 70 includes one or a plurality of linear racks disposed about member 60. In some embodiments, surface 70 includes a rack of teeth circumferentially disposed about member 60.

Member 60 includes an inner sleeve, such as, for example, a sleeve 82 and an outer sleeve, such as, for example, a sleeve 84. Sleeve 82 is configured for moveable disposal within sleeve 84. Sleeve 82 includes one or more capture elements, such as, for example, a capture element 86 and a capture element 88 disposed at end 64. Elements 86, 88 are configured for releasable engagement with connector 150. Elements 86, 88 each include an inner surface that defines an implant cavity configured for disposal of at least a portion of connector 150. The inner surfaces of elements 86, 88 include at least one fixation surface, such as, for example, inward tab projections 90, 92 respectively, configured to releasably capture connector 150. In some embodiments, all or only a portion of the inner surface may have alternate surface configurations to enhance fixation with the implant, such as, for example, dimpled and/or textured. In various embodiments, projections 90, 92 may include a nail configuration, raised elements and/or spikes to facilitate engagement with connector 150.

Sleeve 84 is translatable relative to sleeve 82 to resist and/or prevent expansion of sleeve 82 and disengagement of projections 90, 92 from connector 150. In some embodiments, sleeve 84 includes a flange 85 engageable with spinal rod 170 for selectively locking spinal rod 170 with connector 150. In some embodiments, flange 85 includes an arcuate surface configured to mate and/or fit with an outer surface of spinal rod 170. In some embodiments, sleeve 82 and sleeve 84 may be configured to engage spinal rod 170 for selectively locking spinal rod 170 with connector 150.

In some embodiments, sleeve 84 is actuated by a knob 94. Knob 94 is rotatable to facilitate axial translation of sleeve 84 relative to sleeve 82, as described herein. In some embodiments, knob 94 is threadingly engaged with member 60 such that rotation of knob 94 causes translation of sleeve 84 relative to sleeve 82. Translation of sleeve 84 over sleeve 82 resists and/or prevents disengagement of projections 90, 92 from connector 150. Knob 94 includes a surface 96 configured to facilitate gripping and rotation. In some embodiments, surface 96 may have alternate surface configurations, such as, for example, grooved, rough, threaded for connection with surgical instruments, arcuate, undulating, porous, semi-porous, dimpled, polished and/or textured.

Ratchet 80 includes pawl 100. Pawl 100 includes a gear tooth 102. Gear tooth 102 is configured for engagement with gear teeth 78 of rack 72. Pin 104 connects pawl 100 with an actuator, such as, for example, a lever 106. Pawl 100 is rotatable by lever 106 relative to rack 72 such that pawl 100 pivots about pin 104. Pawl 100 pivots about pin 104 to facilitate releasable engagement of tooth 102 with teeth 78 to translate carriage 18 incrementally relative to member 60 along axis X1. In some embodiments, lever 106 is biased in a first position with a biasing member, such as, for example, a spring arm 108. In the first position, pawl 100 is biased into engagement with rack 72. Lever 106 is configured for actuation between the first position and a second position such that lever 106 causes carriage 18 to axially translate relative to member 60. Actuation of lever 106 is configured to translate carriage 18 in a first direction relative to member 60 to incrementally tension tether 130.

Tether 130 is a flexible longitudinal element that extends between an end 132 and an end 134. Tether 130 is configured for engagement with connector 150, as described herein. In some embodiments, end 132 and end 134 form a loop configured to surround all or a portion of tissue, such as, for example, laminae and/or a spinal implant, such as, for example, a spinal rod 170, as described herein. Tether 130 is configured for tensioning about a targeted portion of an anatomy of a body for attachment of tether 130 with the targeted portion of the anatomy, as described herein. In some embodiments, the targeted portion of the anatomy may include laminae, transverse process and/or pedicle regions of a vertebral level. In some embodiments, spinal correction system 10 may include one or a plurality of tethers 130, each tether being configured for disposal about a single and separate vertebral level. In some embodiments, a single vertebral level may include one or a plurality of tethers 130.

Tether 130 has a flexible configuration and may be fabricated from materials, such as, for example, fabric, silicone, polyurethane, silicone-polyurethane copolymers, polymeric rubbers, polyolefin rubbers, elastomers, rubbers, thermoplastic elastomers, thermoset elastomers and elastomeric composites. In some embodiments, the flexibility of tether 130 includes movement in a lateral or side to side direction and prevents expanding and/or extension in an axial direction upon tensioning and attachment with a targeted portion of the anatomy. In some embodiments, all or only a portion of tether 130 may have a semi-rigid, rigid or elastic configuration, and/or have elastic properties, similar to the material examples described above, such that tether 130 provides a selective amount of expansion or extension in an axial direction. In some embodiments, tether 130 may be compressible in an axial direction. Tether 130 can include a plurality of separately attachable or connectable portions or sections, such as bands or loops, or may be monolithically formed as a single continuous element.

Tether 130 can have a uniform thickness/diameter. In some embodiments, tether 130 may have various surface configurations, such as, for example, smooth and/or surface configurations to enhance fixation, such as, for example, rough, arcuate, undulating, porous, semi-porous, dimpled, polished and/or textured. In some embodiments, the thickness defined by tether 130 may be uniformly increasing or decreasing, or have alternate diameter dimensions along its length. In some embodiments, tether 130 may have various cross section configurations, such as, for example, oval, oblong, triangular, rectangular, square, polygonal, irregular, uniform, non-uniform, variable and/or tapered. In some embodiments, the surface of tether 130 may include engaging structures, such as, for example, barbs, raised elements and/or spikes to facilitate engagement with tissue of the targeted anatomy.

In some embodiments, tether 130 may have various lengths. In some embodiments, tether 130 may be braided, such as a rope, or include a plurality elongated elements to provide a predetermined force resistance. In some embodiments, tether 130 may be made from autograft and/or allograft, and be configured for resorbable or degradable applications. In some embodiments, tether 130 is a cadaver tendon. In some embodiments, tether 130 is a tendon that may be harvested, for example, from a patient or donor. In some embodiments, a tendon harvested from a patient may be affixed in remote locations with the patient's body.

Figure 7:
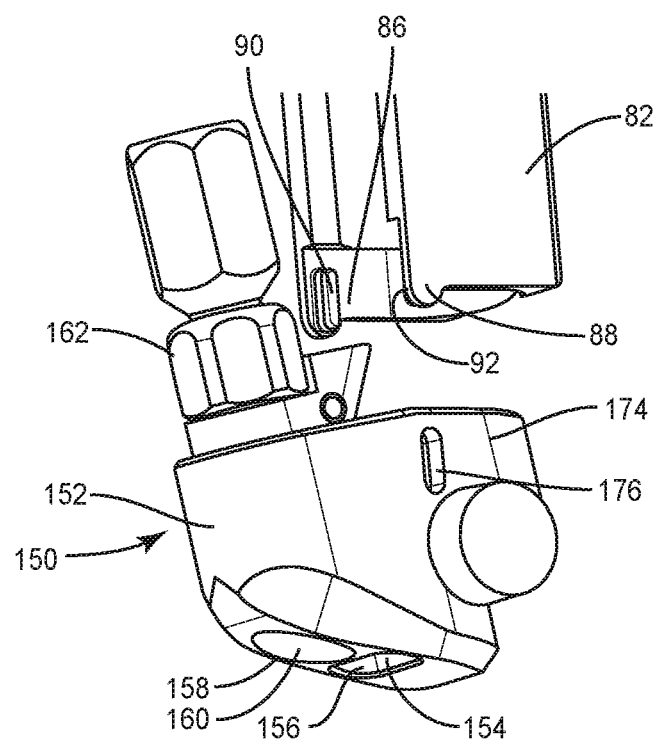
FIG. 7 is a break away perspective view of the components shown in FIG. 6.
Figure 8:
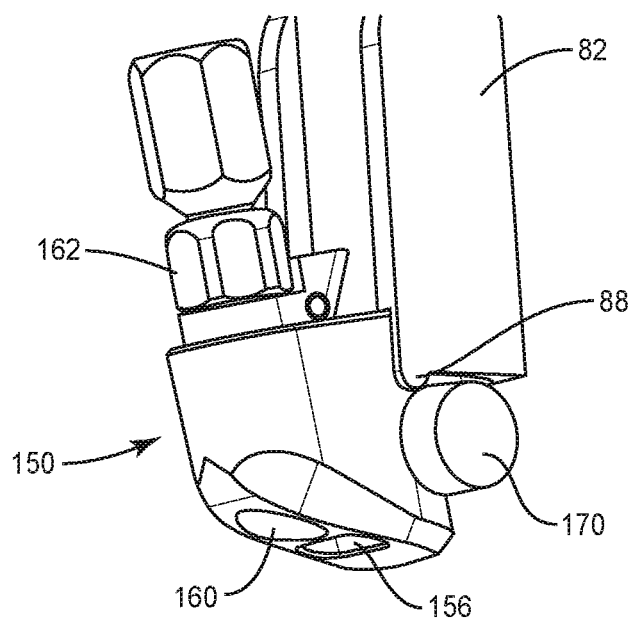
FIG. 8 is a break away perspective view of the components shown in FIG. 6.
Figure 9:
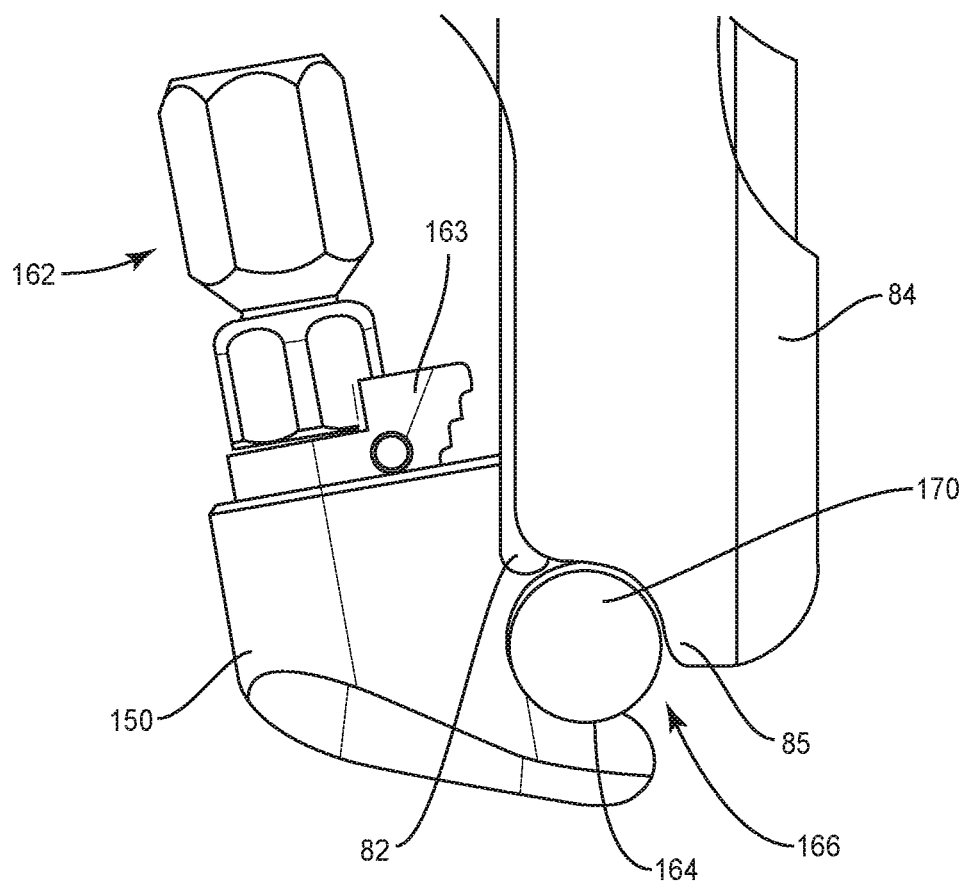
FIG. 9 is a break away side view of the components shown in FIG. 6.

Spinal correction system 10 includes connector 150. Connector 150 includes a body 152 having a surface 154 that defines a cavity, such as, for example, a passageway 156 configured for disposal of tether 130. In some embodiments, passageway 156 may have various cross section configurations, such as, for example, oval, oblong, triangular, rectangular, square, polygonal, irregular, uniform, non-uniform, variable and/or tapered. In some embodiments, surface 154 may include gripping elements or surfaces, such as, for example, rough, arcuate, undulating, mesh, porous, semi-porous, dimpled and/or textured to facilitate engagement with tether 130. Body 152 includes a surface 158 that defines a cavity, such as, for example, an opening 160. Opening 160 is configured for disposal of a coupling member, such as, for example, a set screw 162 (FIGS. 7-9).

Body 152 includes a surface 164 that defines a passageway 166. Passageway 166 has an oblong configuration and extends transversely through body 152. In some embodiments, passageway 166 may have alternate cross section configurations, such as, for example, oval, cylindrical, triangular, square, polygonal, irregular, uniform, non-uniform, offset, staggered, undulating, arcuate, variable and/or tapered. Passageway 166 is configured for disposal of spinal rod 170 such that connector 150 can be mounted with spinal rod 170, as described herein.

Body 152 includes a mating surface 174 that defines cavities, such as, for example, mating slots 176 configured to mate with projections 90, 92 to facilitate connection of tensioner 12 with connector 150, as described herein. In some embodiments, spinal correction system 10 may include one or a plurality of implant connectors spaced apart and disposed along a spinal implant, such as, for example, spinal rod 170, which may be relatively disposed in a side by side, irregular, uniform, non-uniform, offset and/or staggered orientation or arrangement, along one or a plurality of spinal rods. In some embodiments, spinal rod 170 extends along one or a plurality of vertebra, as described herein. In some embodiments, spinal correction system 10 may include one or a plurality of spinal rods 170, which may be relatively disposed in a side by side, irregular, uniform, non-uniform, offset and/or staggered orientation or arrangement.

In assembly, operation and use, spinal correction system 10, similar to the systems and methods described herein, is employed with a surgical procedure, such as, for example, a correction treatment of an affected portion of a spine, which may include a correction treatment to treat adolescent idiopathic scoliosis and/or Scheuermann's kyphosis of a spine. In some embodiments, one or all of the components of spinal correction system 10 can be delivered or implanted as a pre-assembled device or can be assembled in situ. Spinal correction system 10 may be completely or partially revised, removed or replaced.

In use, to treat a selected section of vertebrae V, as shown in FIG. 10, a medical practitioner obtains access to a surgical site including vertebrae V in any appropriate manner, such as through incision and retraction of tissues. In some embodiments, spinal correction system 10 can be used in any existing surgical method or technique including open surgery, mini-open surgery, minimally invasive surgery and percutaneous surgical implantation, whereby vertebrae V is accessed through a mini-incision, or a sleeve that provides a protected passageway to the area. Once access to the surgical site is obtained, the particular surgical procedure can be performed for treating the spine disorder.

An incision is made in the body of a patient and a cutting instrument (not shown) creates a surgical pathway for implantation of components of spinal correction system 10. A preparation instrument (not shown) can be employed to prepare tissue surfaces of vertebrae V, as well as for aspiration and irrigation of a surgical region.

Tether 130 is delivered along the surgical pathway to a surgical site adjacent a lateral side of vertebrae V. Tether 130 is disposed with vertebrae V and/or spinal rod 170. In one embodiment, as shown in FIG. 10, a loop 136 of tether 130 is disposed about a transverse process of a vertebra. This configuration fixes and/or attaches tether 130 with the transverse process and/or lamina.

Tensioner 12 is disposed adjacent connector 150. Sleeve 82 is disposed adjacent connector 150 such that projections 90, 92 engage mating slots 176. Knob 94 is rotated, in a clockwise direction shown by arrow A in FIG. 6, to translate sleeve 84 relative to sleeve 82 such that sleeve 84 slides over sleeve 82 to resist and/or prevent disengagement of sleeve 82 from connector 150. Connector 150 is positioned adjacent spinal rod 170 such that spinal rod 170 is disposed in passageway 166. In some embodiments, sleeve 82 and/or sleeve 84 engages spinal rod 170 to lock spinal rod 170 in position with connector 150, as described herein. Tether 130 is threaded through pathway 28 of tensioner 12.

Tether 130 is threaded through passageway 156 for connection with connector 150. Screw 162 is disposed in a non-locked orientation such that tether 130 is movable within passageway 156 and a cleat 163 is positioned therein.

Lever 30 is disposed in the non-locked orientation, as shown in phantom in FIG. 2. Lever 30 is actuated to pivot, in a direction shown by arrow B in FIG. 10, such that locking surface 38 engages tether 130, as described herein, to dispose lever 30 in the locked orientation. Locking surface 38 applies a compression force to tether 130 to resist and/or prevent tether 130 from freely translating and/or disengaging from pathway 28. Latch 36 pivots to capture lever 30 within cavity 48 to resist and/or prevent lever 30 from pivoting, in a direction shown by arrow C, to a release position and/or allowing tether 130 to freely translate and/or disengage from pathway 28.

Lever 106 is biased in the first position, as shown in FIG. 3, such that carriage 18 is fixed with member 60 at a selected height. Lever 106 is actuated via a compression force applied to lever 106, as shown by arrow D in FIG. 10, to overcome the bias of spring arm 108 causing lever 106 to move to the second position. In the second position, pawl 100 pivots about pin 104. Gear teeth 78 are oriented with tooth 102 such that pivoting of pawl 100 causes gear tooth 102 to disengage from and slide over gear teeth 78 facilitating translation of carriage 18, in a direction shown by arrow E in FIG. 10, to advance carriage 18 relative to member 60 to a selected height. Upon incremental advancement of tooth 102 with a successive tooth of teeth 78, teeth 78 are oriented with tooth 102 such that tooth 102 abuts an adjacent tooth of teeth 78 to resist and/or prevent translation of carriage 18 in an opposing direction, for example, in a direction shown by arrow F.

Actuation of lever 106 causes axial translation of carriage 18 in a direction along axis X1 and relative to member 60 to tension tether 130. Pivoting catch 52 engages gear teeth 78 to resist and/or prevent axial translation of carriage 18, in a direction shown by arrow F.

Translation of carriage 18 draws tether 130 to apply a tensioning force to tether 130. This configuration tensions tether 130 about the vertebra and tensions the spinal construct for attachment with vertebrae V and/or to apply corrective treatment to vertebrae V. In some embodiments, the tension and/or tensile force applied to tether 130 and/or corrective forces applied to vertebrae V can be increased by further actuation of lever 106 to incrementally and/or selectively tension tether 130. In some embodiments, the tension and/or tensile force applied to tether 130 and/or corrective forces applied to vertebrae V can be increased and/or decreased by tensioner 12.

Screw 162 is actuated by a driver (not shown) by rotating screw 162 in a clockwise direction to engage cleat 163. Cleat 163 is translated within passageway 156 such that its teeth engage tether 130. Translation of cleat 163 applies a compressive force and/or a friction force to fix tether 20 in a locked orientation with connector 150. In some embodiments, the driver is rotated to a predetermined force and/or torque limit to separate frangible portions of screw 162. This configuration fixes tension of tether 130 about vertebrae V and tensions components of the spinal construct for attachment with vertebrae V and/or to apply corrective treatment to vertebrae V.

To disengage tensioner 12 from connector 150, knob 94 is rotated in a counter clockwise direction, as shown by arrow G in FIG. 6. Sleeve 84 translates in an opposite direction relative to sleeve 82 to facilitate disengagement of projections 90, 92 from connector 150 and release of the components of tensioner 12 from the spinal construct.

Spinal rod 170 is disposed with passageway 166. A set screw (not shown) is engaged with an opening of connector 150 to fix spinal rod 170 with connector 150 and for attachment of spinal rod 170 with vertebrae V via tether 130.

In some embodiments, spinal implant system 10 includes a second spinal rod 170 (not shown) delivered along the surgical pathway to the surgical site adjacent a contra-lateral side of vertebrae V. Second spinal rod 170 is connected with the contra-lateral side of vertebrae V via one or more tethers 130, similar to spinal rod 170 described herein. In some embodiments, spinal rod 170 and second spinal rod 170 are fixed with vertebrae V in a side by side orientation and/or a bi-lateral arrangement to stabilize vertebrae V and affect growth for a correction treatment to treat spine pathologies, as described herein. In some embodiments, one or all of the components of spinal implant system 10 can be delivered or implanted as a pre-assembled device or can be assembled in situ, in a selected order of assembly or the order of assembly of the particular components of system 10 can be varied according to practitioner preference, patient anatomy or surgical procedure parameters. Spinal implant system 10 may be completely or partially revised, removed or replaced.

Upon completion of the procedure, the surgical instruments, assemblies and non-implanted components of spinal correction system 10 are removed from the surgical site and the incision is closed. One or more of the components of spinal correction system 10 can be made of radiolucent materials such as polymers. Radiomarkers may be included for identification under x-ray, fluoroscopy, CT or other imaging techniques. In some embodiments, the use of surgical navigation, microsurgical and image guided technologies may be employed to access, view and repair spinal deterioration or damage, with the aid of spinal correction system 10.

In some embodiments, spinal correction system 10 includes an agent, which may be disposed, packed, coated or layered within, on or about the components and/or surfaces of spinal correction system 10. In some embodiments, the agent may include bone growth promoting material, such as, for example, bone graft to enhance fixation of the bone fasteners with vertebrae. In some embodiments, the agent may include one or a plurality of therapeutic agents and/or pharmacological agents for release, including sustained release, to treat, for example, pain, inflammation and degeneration.

In some embodiments, the components of spinal correction system 10 may be employed to treat progressive idiopathic scoliosis with or without sagittal deformity in either infantile or juvenile patients, including but not limited to prepubescent children, adolescents from 10-12 years old with continued growth potential, and/or older children whose growth spurt is late or who otherwise retain growth potential. In some embodiments, the components of spinal correction system 10 may be used to prevent or minimize curve progression in individuals of various ages.

Figure 11:
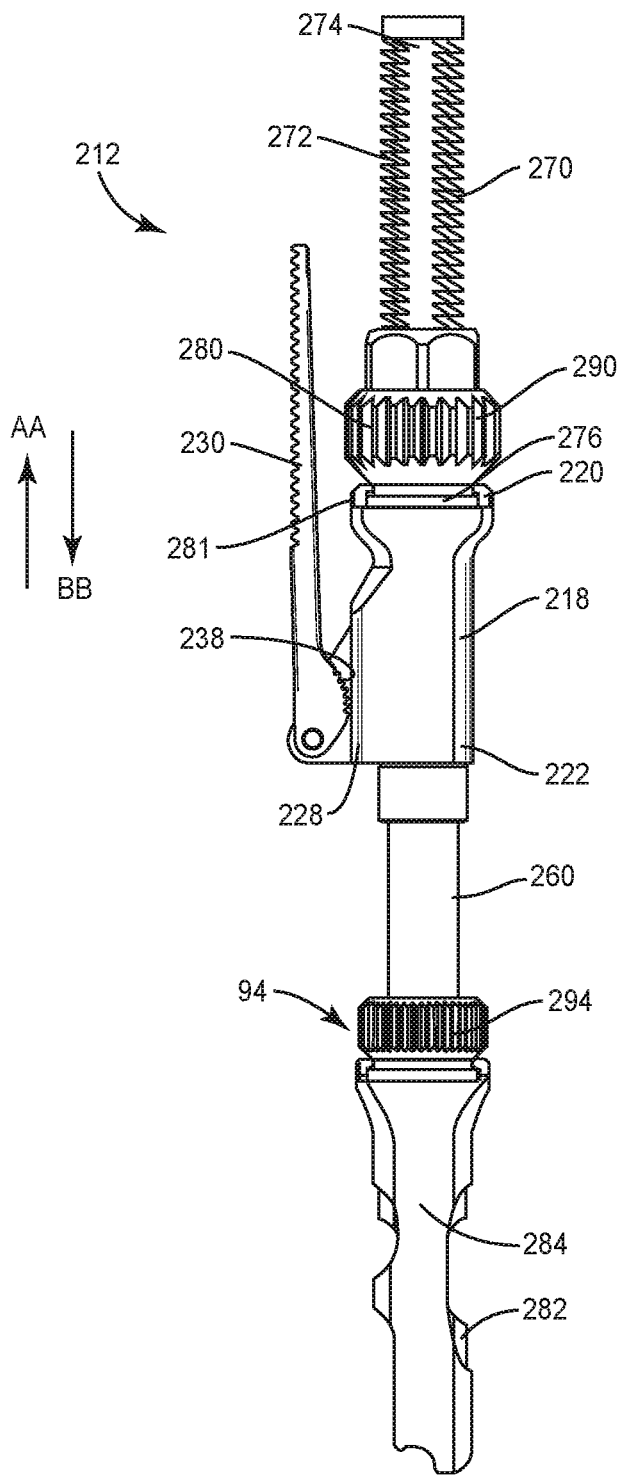
FIG. 11 is a side view of one embodiment of components of a surgical system in accordance with the principles of the present disclosure.
Figure 12:
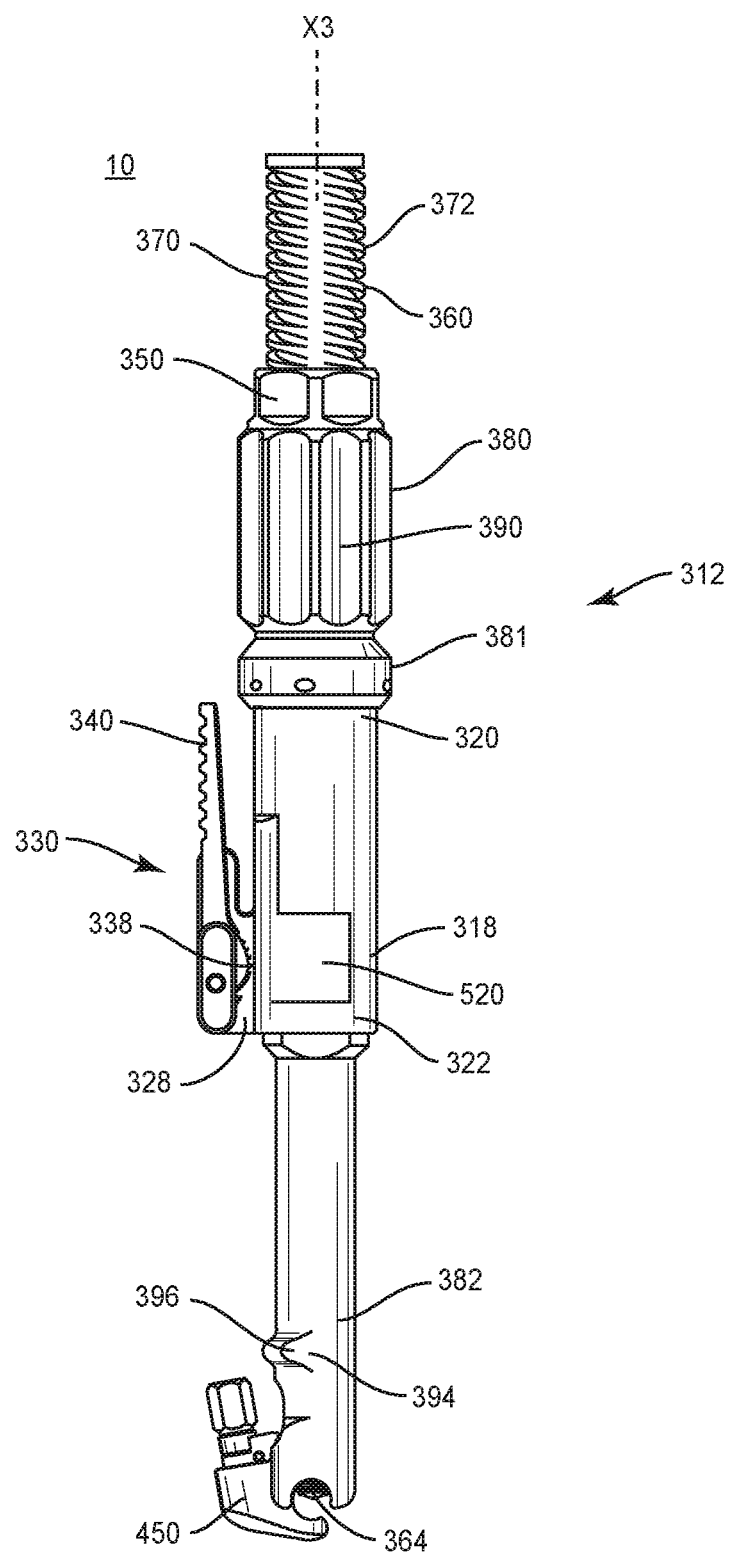
FIG. 12 is a side view of one embodiment of components of a surgical system in accordance with the principles of the present disclosure.
Figure 13:
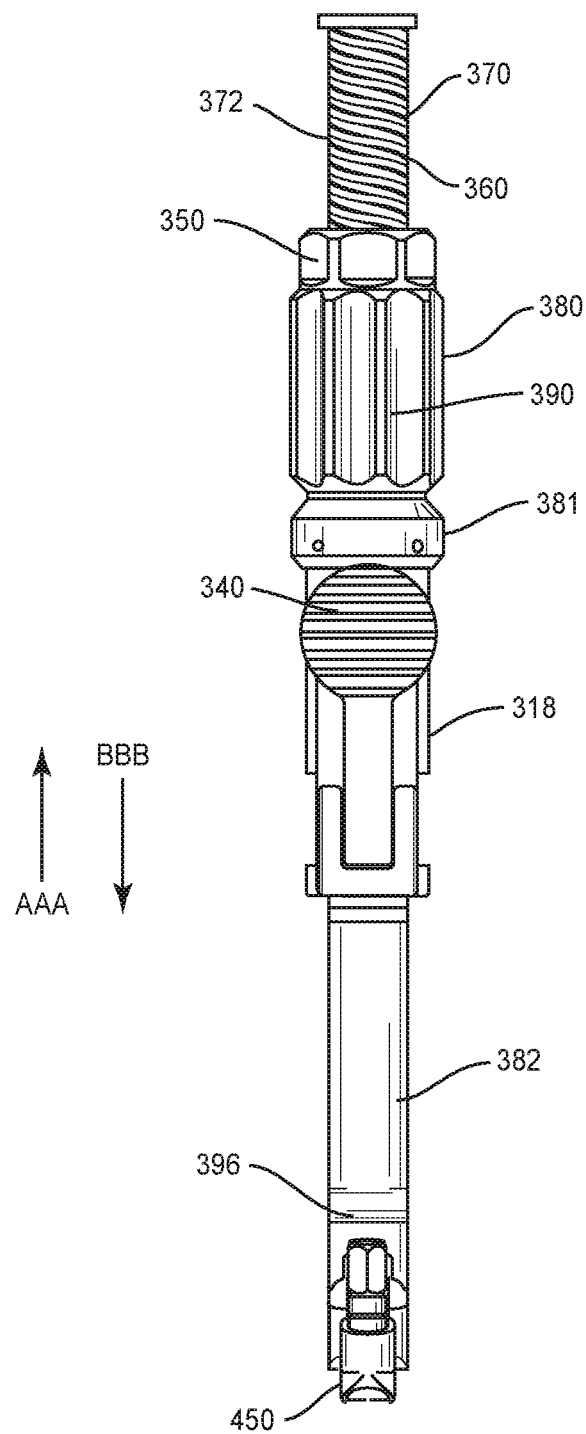
FIG. 13 is a side view of the components shown in FIG. 12.
Figure 14:
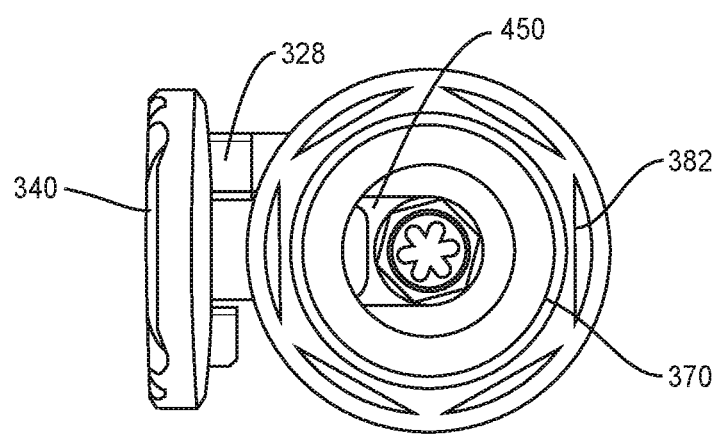
FIG. 14 is an end view of the components shown in FIG. 12.
Figure 15:
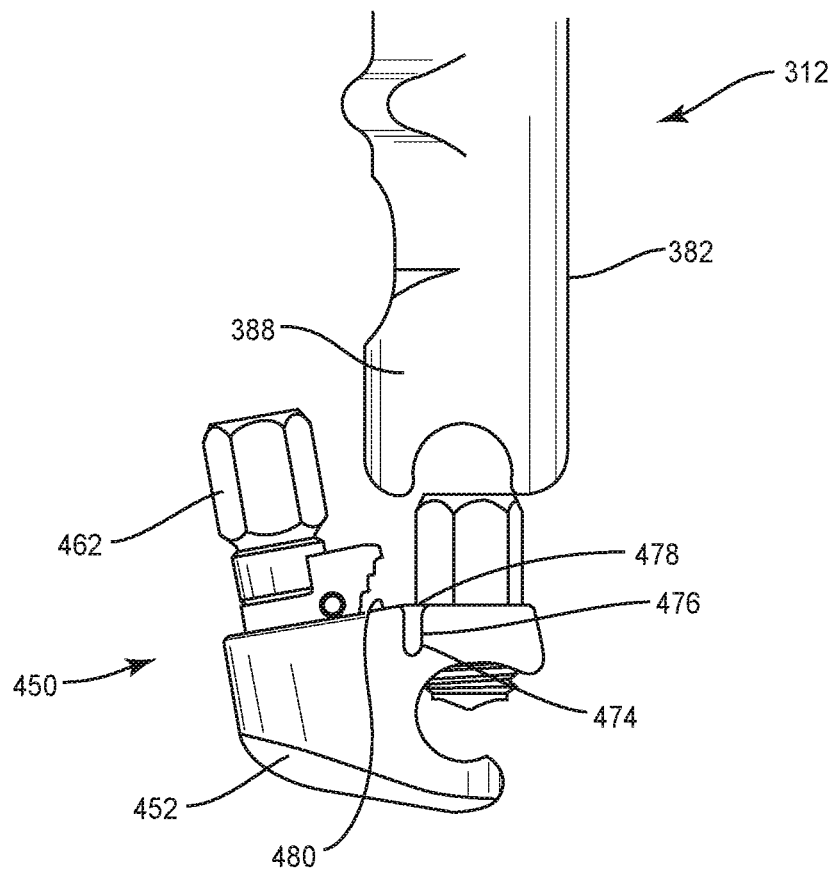
FIG. 15 is a break away view of the components shown in FIG. 12.
Figure 16:
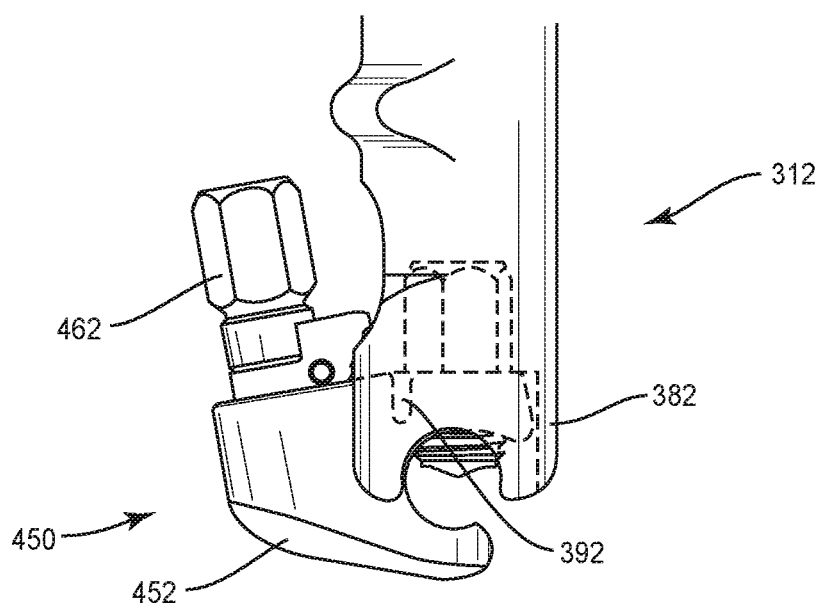
FIG. 16 is a break away view of the components shown in FIG. 12.
Figure 17:
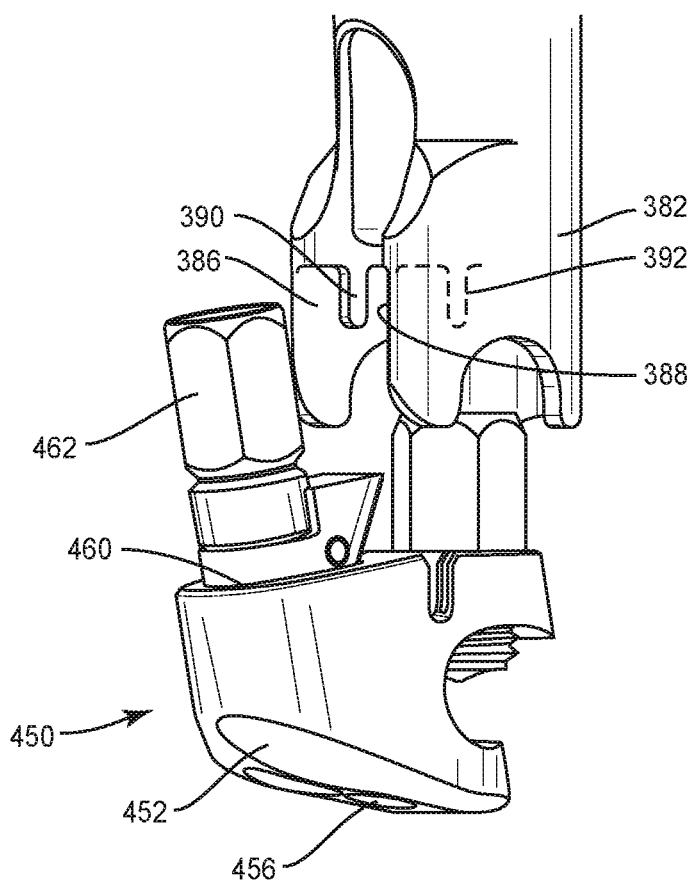
FIG. 17 is a break away view of the components shown in FIG. 12.
Figure 18:
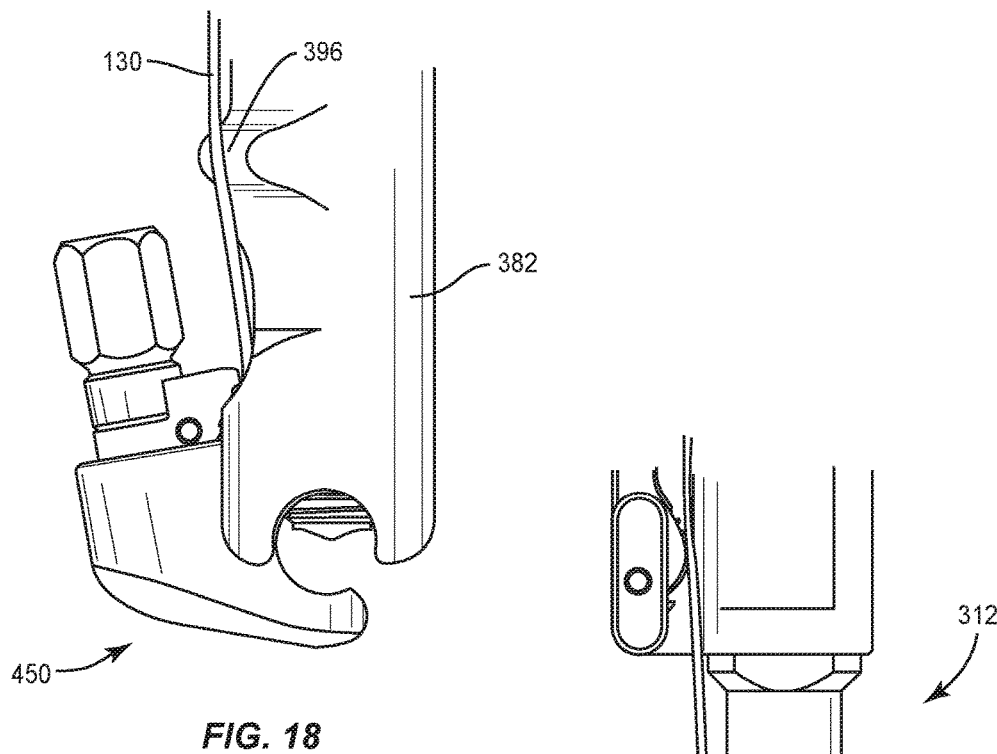
FIG. 18 is a break away side view of one embodiment of components of a surgical system in accordance with the principles of the present disclosure.
Figure 19:
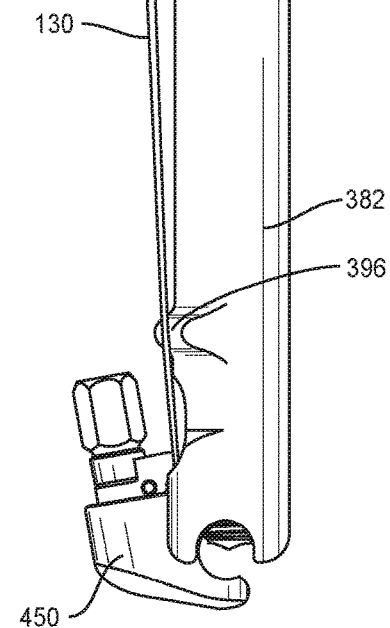
FIG. 19 is a side view of the components shown in FIG. 18.

In one embodiment, as shown in FIG. 11, spinal correction system 10, similar to the systems and methods described above with regard to FIGS. 1-10, includes a tensioner 212, similar to tensioner 12 described herein. Tensioner 212 includes a carriage 218, similar to carriage 18 described herein. Carriage 218 extends between an end 220 and an end 222, and defines a longitudinal axis.

Carriage 218 defines a pathway 228, similar to pathway 28 described herein, and is configured for disposal of tether 130, as described herein. Carriage 218 includes a lever 230, similar to lever 30 described herein. In some embodiments, lever 230 is employed with latch 36 described herein. Lever 230 includes a locking surface 238, similar to surface 38 described herein. Lever 230 pivots to facilitate engagement of locking surface 238 with tether 130 to resist and/or prevent disengagement of tether 130 from pathway 228, as described herein. Rotation of lever 230 causes locking surface 238 to pivot between a non-locked orientation and a locked orientation relative to tether 130. Locking surface 238 applies a compressive force and/or a friction force, as described herein, to fix tether 130 in the locked orientation.

Tensioner 212 includes a member 260, similar to member 60 described herein. Member 260 includes an outer surface 270 that includes a threaded surface 272. Threaded surface 272 extends between an end 274 and an end 276. In some embodiments, threaded surface 272 is continuous along surface 270. In some embodiments, threaded surface 272 may include a single thread turn, spaced apart threads or a plurality of discrete threads. In some embodiments, threaded surface 272 includes one or more racks, as described herein.

Threaded surface 272 is configured for engagement with an actuator, such as, for example, a knob 280. Knob 280 includes a surface 290 configured to facilitate gripping and rotation. In some embodiments, surface 290 may have alternate surface configurations, such as, for example, grooved, rough, threaded for connection with surgical instruments, arcuate, undulating, porous, semi-porous, dimpled, polished and/or textured.

Member 260 includes a circumferential flange 281 that movably supports knob 280. A threaded inner surface of knob 280 engages threaded surface 272 such that knob 280 is rotatable relative to flange 281 to axially translate member 260, in a direction shown by arrow AA and a direction shown by arrow BB, relative to carriage 218. Knob 280 is rotatable in a clockwise and a counter clockwise direction to facilitate axial translation of carriage 218 relative to member 260, similar to that described herein. Translation of carriage 218 relative to member 260 causes an increase and/or a decrease in tension and/or tensile force in tether 130, as described herein. In some embodiments, carriage 218 is translated relative to member 260, as described, to incrementally increase and/or decrease tension in tether 130. In some embodiments, carriage 218 is translated relative to member 260, as described, to continuously increase and/or decrease tension in tether 130.

Member 260 includes a sleeve 282 and a sleeve 284, similar to sleeves 82, 84 described herein. Sleeves 282, 284 are configured to facilitate connection with connector 150 and/or spinal rod 170, as described herein. Relative translation of sleeves 282, 284 is actuated with a knob 294, similar to knob 94 described herein.

In one embodiment, as shown in FIGS. 12-19, spinal correction system 10, similar to the systems and methods described above with regard to FIGS. 1-10, includes a tensioner 312, similar to the tensioners described herein. Tensioner 312 includes a carriage 318, similar to carriage 18 described herein. Carriage 318 extends between an end 320 and an end 322, and defines a longitudinal axis X3.

Carriage 318 defines a pathway 328, similar to pathway 28 described herein, and is configured for disposal of tether 130, as described herein. Carriage 318 includes a lever 330, similar to lever 30 described herein. In some embodiments, lever 330 is employed with latch 36, as described herein. Lever 330 includes a locking surface 338, similar to surface 38 described herein. Lever 330 pivots to facilitate engagement of locking surface 338 with tether 130 to resist and/or prevent disengagement of tether 130 from pathway 328, as described herein. Rotation of lever 330 causes locking surface 338 to pivot between a non-locked orientation and a locked orientation relative to tether 130. Locking surface 338 applies a compressive force and/or a friction force, as described herein, to fix tether 130 in the locked orientation. In some embodiments, lever 330 includes an enlarged engagement surface 340 configured to facilitate pivoting of lever 330. In some embodiments, lever 330 includes a shorter length to adjust a mechanical advantage of lever 330.

Tensioner 312 includes a member 360, similar to member 60 described herein. Member 360 includes an outer surface 370 that includes a threaded surface 372. Threaded surface 372 extends between an end 374 and an end 376. In some embodiments, threaded surface 372 is continuous along surface 370. In some embodiments, threaded surface 372 includes a triple thread turn, spaced apart threads or a plurality of discrete threads. In some embodiments, threaded surface 372 includes one or more racks, as described herein. In some embodiments, indicia, such as, for example, hash marks are disposed on surface 370 to provide reference of dimension, such as, for example, length, depth and/or height.

Threaded surface 372 is configured for engagement with an actuator, such as, for example, a knob 380. Knob 380 includes a surface 390 configured to facilitate gripping and rotation of knob 380. In some embodiments, surface 390 may have alternate surface configurations, such as, for example, grooved, rough, threaded for connection with surgical instruments, arcuate, undulating, porous, semi-porous, dimpled, polished and/or textured. In some embodiments, knob 380 includes a surface, such as, for example, a tool engaging surface 350. Tool engaging surface 350 is configured for a mating engagement with a tool, such as, for example, a socket driver 500, as described herein. In some embodiments, tool engaging surface 350 includes configurations, such as, for example, triangular, square, polygonal, hexalobular, star or torx.

Member 360 includes a circumferential flange 381 that movably supports knob 380. A threaded inner surface of knob 380 engages threaded surface 372 such that knob 380 is rotatable relative to flange 381 to axially translate member 360, in a direction shown by arrow AAA in FIG. 13 and a direction shown by arrow BBB, relative to carriage 318. Knob 380 is rotatable in a clockwise and a counter clockwise direction to facilitate axial translation of carriage 318 relative to member 360, similar to that described herein. Translation of carriage 318 relative to member 360 causes an increase and/or a decrease in tension and/or tensile force in tether 130, as described herein. In some embodiments, carriage 318 is translated relative to member 360, as described, to incrementally increase and/or decrease tension in tether 130. In some embodiments, carriage 318 is translated relative to member 360, as described, to continuously increase and/or decrease tension in tether 130.

Member 360 includes a sleeve 382 having one or more capture elements, such as, for example, a capture element 386 and a capture element 388 disposed at an end 364. Elements 386, 388 are configured for releasable engagement with connector 450. Elements 386, 388 each include an inner surface that defines an implant cavity configured for disposal of at least a portion of connector 450, as described herein. The inner surfaces of elements 386, 388 include at least one fixation surface, such as, for example, inward tab projections 390, 392 respectively, configured to releasably capture connector 450. Projections 390, 392 extend axially along sleeve 382.

Sleeve 382 includes a surface 394 that defines a projection 396. Projection 396 includes an arcuate surface 398 configured to facilitate straightening of tether 130 during tensioning. Surface 398 is configured to prevent tether 130 from contacting any surfaces that would damage and/or tear tether 130. In some embodiments, surface 398 may have alternate surface configurations, such as, for example, grooved, undulating, porous, semi-porous, dimpled, polished and/or textured.

Spinal correction system 10 includes connector 450, similar to connector 150 described herein. Connector 450 includes a body 452 having a passageway 456, similar to passageway 156 described herein, configured for disposal of tether 130. Body 452 includes an opening 460, similar to opening 160 described herein, configured for disposal of a coupling member, such as, for example, a set screw 462. Body 452 includes a passageway 466, similar to passageway 166 described herein, configured for disposal of spinal rod 170 such that connector 450 can be mounted with spinal rod 170, as described herein.

Body 452 includes a mating surface 474 that defines cavities, such as, for example, mating slots 476 configured to mate with projections 390, 392 to facilitate connection of tensioner 312 with connector 450, as described herein. Mating slots 476 are disposed on opposite sides of connector 450 and each include an opening 478 oriented towards a top surface 480 of connector 450. Openings 478 are configured to axially guide projections 390, 392 into mating slots 476. Mating slots 476 are configured to provide docking for tensioner 312 with connector 450.

Figure 20:
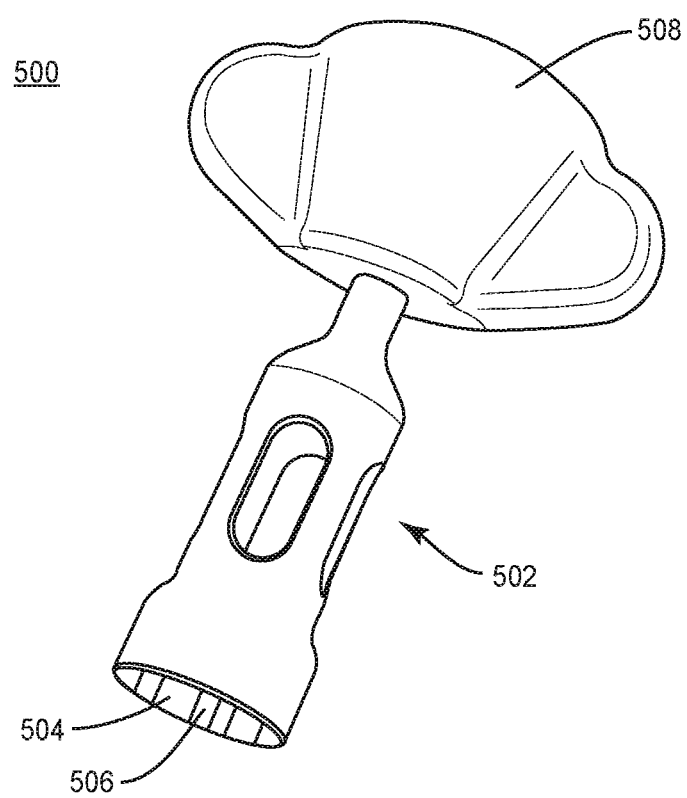
FIG. 20 is a perspective view of one embodiment of components of a surgical system in accordance with the principles of the present disclosure.

In some embodiments, as shown in FIG. 20, spinal correction system 10 includes a driver 500 that includes a body 502. Body 502 includes a surface 504 that defines a cavity 506. Surface 504 is configured for mating engagement with tool engaging surface 350. Cavity 506 is centrally positioned relative to driver 500. In some embodiments, cavity 506 may include a square, triangular, hexagonal, polygonal, star, torx or hexalobe cross section such that surface 504 is configured to engage a correspondingly shaped portion of tool engaging surface 350. In some embodiments, cavity 506 may have various cross-section configurations, such as, for example, oval, oblong, triangular, rectangular, square, polygonal, irregular, uniform, non-uniform, variable, tubular and/or tapered. In some embodiments, surface 504 may have various surface configurations to facilitate engagement with tool engaging surface 350, such as, for example, rough, arcuate, undulating, porous, semi-porous, dimpled, polished and/or textured.

Figure 21:
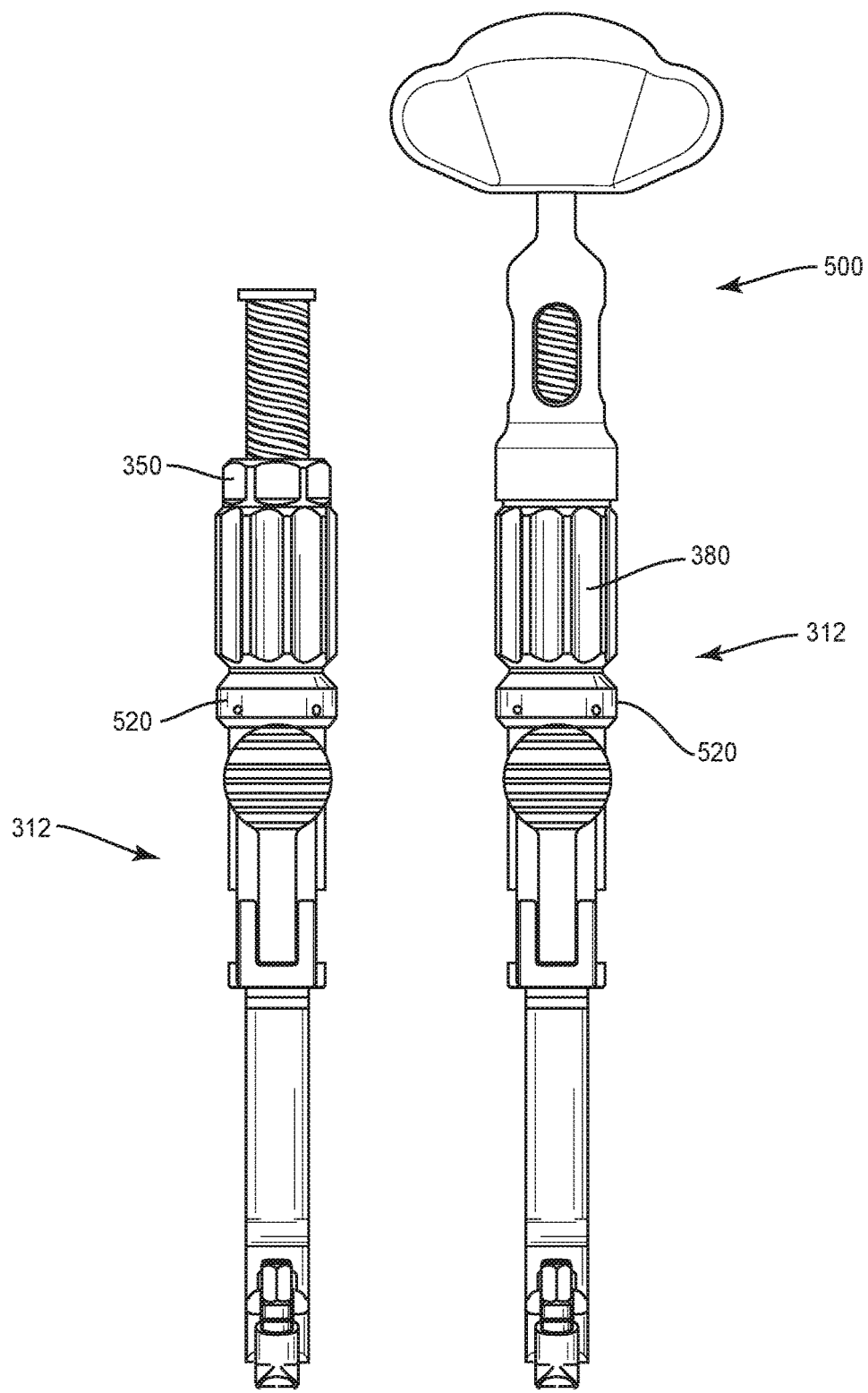
FIG. 21 is a side view of one embodiment of components of a surgical system in accordance with the principles of the present disclosure.

Driver 500 includes a handle 508 configured to facilitate manipulation of driver 500. In some embodiments, handle 508 includes a T-shape with body 502. In some embodiments, handle 506 may be disposed at alternate orientations relative to body 502, such as, for example, transverse, perpendicular and/or other angular orientations such as acute or obtuse. Driver 500 is configured to provide torque to knob 380 to facilitate tensioning of tether 130. In some embodiments, driver 500 facilitates segmental tensioning of tether 130 when multiple tensioners 312 are utilized, as shown in FIG. 21.

Figure 22:
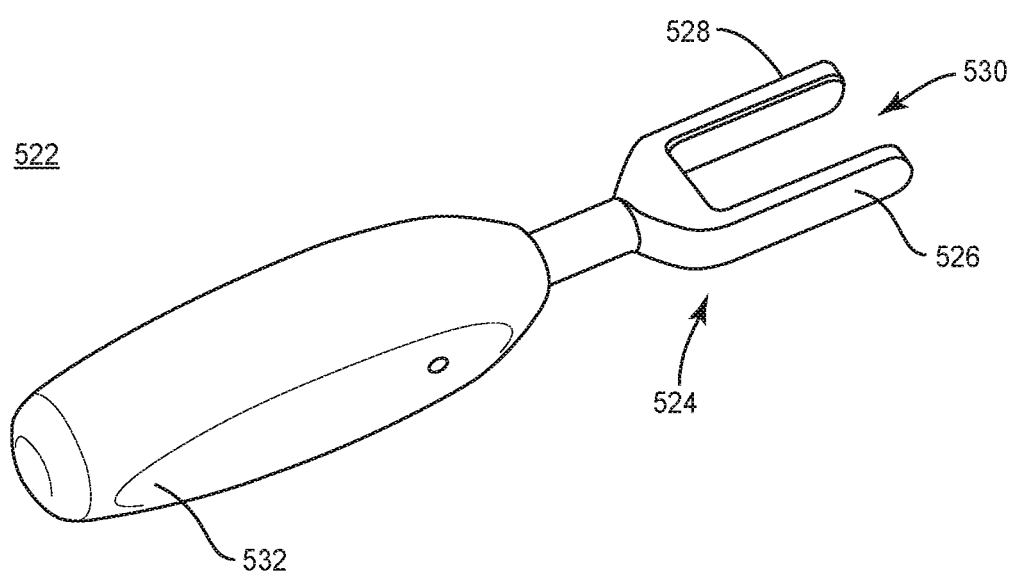
FIG. 22 is a perspective view of one embodiment of components of a surgical system in accordance with the principles of the present disclosure.
Figure 23:
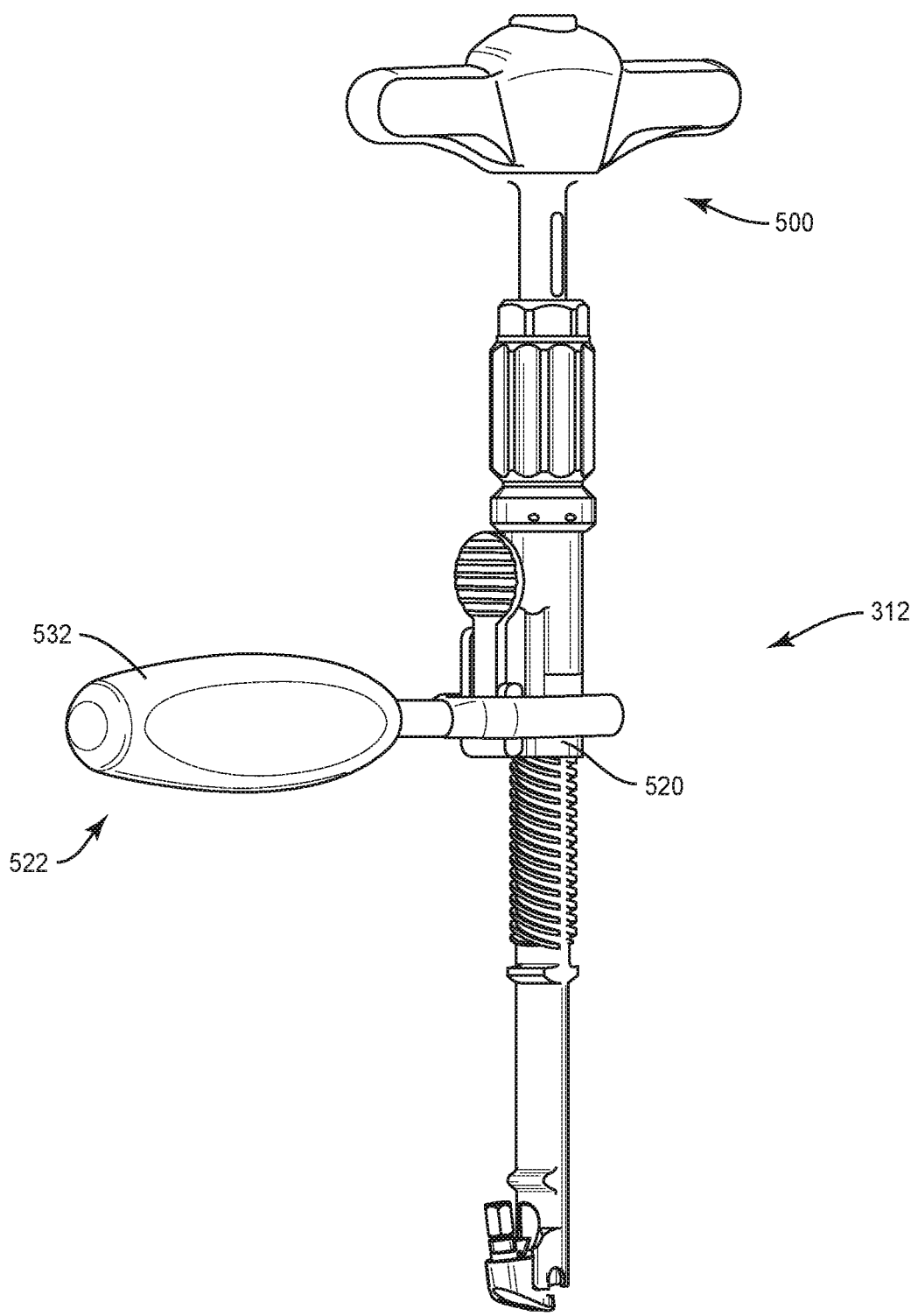
FIG. 23 is a side view of one embodiment of components of a surgical system in accordance with the principles of the present disclosure.

In some embodiments, carriage 318 includes a surface, such as, for example, a tool engaging surface 520. In some embodiments, as shown in FIGS. 22 and 23, tool engaging surface 520 is configured for mating engagement with a tool, such as, for example, a counter torque tool 522 of spinal correction system 10, as described herein. In some embodiments, tool engaging surface 520 includes alternate configurations, such as, for example, triangular, square, polygonal cross section for engaging a correspondingly shaped portion of counter torque handle 522.

Counter torque tool 522 includes a body 524. Body 524 includes a pair of spaced apart arms 526, 528 that define a cavity 530. Cavity 530 is configured for mating engagement with tool engaging surface 520. In some embodiments, cavity 530 may include a square, triangular, hexagonal, polygonal cross section configured to engage a correspondingly shaped portion of tool engaging surface 520. Counter torque tool 522 includes a handle 532 configured to facilitate manipulation of counter torque tool 522. In some embodiments, handle 532 may be disposed at alternate orientations relative to body 524, such as, for example, coaxially, transverse, perpendicular and/or other angular orientations such as acute or obtuse. In some embodiments counter torque tool

522 is configured to provide additional leverage to facilitate removing and/or separating frangible or break off portions of set screws engaged with a connector at a selected torque limit, as described herein.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A surgical instrument comprising:
    a first member defining a channel and a cavity and including a locking surface disposed with the cavity, the locking surface being engageable with a longitudinal member to fix the longitudinal member with the first member;
    a second member including a first end having a rack and a second end having at least one mating element engageable with a spinal construct, the rack being positioned within the channel; and
    an actuator connected with the members and being configured to incrementally tension the longitudinal member, the actuator comprising a gear tooth engageable with teeth of the rack to prevent translation of the first member relative to the second member.

2. A surgical instrument as recited in claim 1, wherein the actuator is configured to pivot relative to the members to disengage the gear tooth from the teeth to cause axial translation of the first member relative to the second member.

3. A surgical instrument as recited in claim 1, wherein the actuator is spring loaded.

4. A surgical instrument as recited in claim 1, wherein the actuator is biased by a spring arm to a configuration in which the gear tooth engages at least one of the teeth.

5. A surgical instrument as recited in claim 1, wherein the actuator is movable between a first configuration in which the gear tooth engages at least one of the teeth and a second configuration in which the gear tooth is spaced apart from the teeth.

6. A surgical instrument as recited in claim 1, wherein the actuator includes a lever that is pivotable relative to the members and an arm that is pivotable relative to the lever about a pin that extends through the arm and the lever, the arm including the gear tooth.

7. A surgical instrument as recited in claim 6, wherein the lever is movable between a first configuration in which the gear tooth engages at least one of the teeth and a second configuration in which the gear tooth is spaced apart from the teeth, the lever being biased to the first configuration by a spring arm.

8. A surgical instrument as recited in claim 1, wherein the first member includes an arm that is pivotable relative to a body of the first member, the arm including the locking surface.

9. A surgical instrument as recited in claim 8, wherein the first member includes a latch that is pivotable relative to the body, the lever including teeth configured to engage the latch to fix the arm relative to the body.

10. A surgical instrument as recited in claim 1, wherein the locking surface includes a plurality of teeth.

11. A surgical instrument as recited in claim 1, wherein the actuator is rotatable to axially translate the first member relative to the second member.

12. A surgical instrument as recited in claim 1, wherein the first member is threaded with the second member.

13. A surgical instrument as recited in claim 1, wherein the first member includes a rotatable cam including the locking surface.

14. A surgical instrument as recited in claim 13, wherein the first member includes a latch engageable with the cam to fix cam position.

15. A surgical instrument as recited in claim 1, wherein the cavity includes a longitudinal member path.

16. A surgical instrument as recited in claim 1, wherein the at least one mating element includes at least one tab configured to engage at least one slot of the spinal construct.

17. A surgical instrument as recited in claim 1, wherein the second member includes an outer sleeve and an inner sleeve.

18. A surgical instrument as recited in claim 17, further comprising a knob that is threadingly engaged with the second member such that rotation of the knob causes translation of the outer sleeve relative to the inner sleeve.

19. A surgical instrument comprising:
    a carriage defining a channel and a pathway and including a locking surface disposed with the pathway, the locking surface being engageable with a longitudinal member to fix the longitudinal member with the carriage;
    a member including a rack, an outer sleeve engageable with a spinal construct and an inner sleeve including at least one mating element engageable with the spinal construct, the at least one mating element being fixed relative to a body of the inner sleeve, the rack being positioned within the channel; and
    a ratchet connected with the carriage and the member that incrementally tensions the longitudinal member, the ratchet comprising a gear tooth engageable with teeth of the rack to prevent translation of the carriage relative to the member.

20. A surgical system comprising:
    a flexible tether;
    a connector configured for disposal of the tether;
    a spinal rod configured for disposal with the connector; and
    a surgical instrument including a first member defining a cavity and including a locking surface disposed with the cavity, the locking surface being engageable with the tether to fix the tether with the first member, a second member including at least one mating element engageable with the connector and an actuator connected with the members that incrementally tensions the tether.

* * * * *